US006638769B2

(12) United States Patent
Lilja et al.

(10) Patent No.: US 6,638,769 B2
(45) Date of Patent: Oct. 28, 2003

(54) ANALYSIS METHOD AND CUVETTE THEREFOR

(75) Inventors: Jan Lilja, Helsingborg (SE); Sven-Erik Nilsson, Nyhamnsläge (SE); Johnny Svensson, Ängelholm (SE); Annika Eriksson, Helsingborg (SE)

(73) Assignee: Migrata UK Ltd., Cy-Limassol (CY)

( * ) Notice: Subject to any disclaimer, the term of this patent is extended or adjusted under 35 U.S.C. 154(b) by 0 days.

(21) Appl. No.: 09/972,918

(22) Filed: Oct. 10, 2001

(65) Prior Publication Data

US 2002/0058342 A1 May 16, 2002

Related U.S. Application Data

(63) Continuation-in-part of application No. 09/711,939, filed on Nov. 15, 2000, now abandoned, which is a continuation of application No. PCT/SE01/01442, filed on Jun. 25, 2001.

(30) Foreign Application Priority Data

Jun. 28, 2000 (SE) ............................... 0002443

(51) Int. Cl.[7] ............................... G01N 33/72
(52) U.S. Cl. .................. 436/66; 436/164; 436/165; 436/166; 422/58; 422/82.05; 422/82.09; 422/102; 422/939
(58) Field of Search ............................. 436/63, 66, 164, 436/165, 166; 422/58, 82.05, 82.09, 99, 102, 939, 940

(56) References Cited

U.S. PATENT DOCUMENTS

| 4,088,448 A | 5/1978 | Lilja et al. |
| 4,255,385 A | 3/1981 | Stroupe et al. |
| 4,275,031 A | 6/1981 | Fischer et al. |
| 4,565,688 A | * 1/1986 | Malin et al. ................... 435/34 |
| 4,654,197 A | 3/1987 | Lilja et al. |
| 5,064,282 A | 11/1991 | Curtis |
| 5,286,454 A | 2/1994 | Nilsson et al. |
| 5,472,671 A | 12/1995 | Nilsson et al. |
| 5,589,393 A | 12/1996 | Fiechtner et al. |
| 5,674,457 A | 10/1997 | Williamsson et al. |
| 5,866,349 A | 2/1999 | Lilja et al. |
| 6,096,552 A | 8/2000 | Nilsson et al. |
| 6,333,007 B1 | 12/2001 | Svensson et al. |

FOREIGN PATENT DOCUMENTS

| JP | 19910303596 | 6/1993 |
| WO | 02/01195 | * 1/2002 |

OTHER PUBLICATIONS

H. von Schenck et al., Evaluation of 'HemoCue,' A New Device for Determining Hemoglobin, *Clinical Chemistry*, vol. 32, No. 3, 1986, pp. 526–528.

* cited by examiner

Primary Examiner—Maureen M. Wallenhorst
(74) Attorney, Agent, or Firm—Burns, Doane, Swecker & Mathis, L.L.P.

(57) ABSTRACT

A method for hemoglobin determination is described which includes the steps of introducing a sample of undiluted whole blood by capillary action into a disposable microcuvette having at least one cavity for receiving the sample. The cavity includes a dry essentially non-hygroscopic hemolysing agent, which is dissolved by the blood, hemolyses the red blood cells and releases the haemoglobin contained in the blood cells. A first absorption measurement at a wavelength range 490–520 nm is then performed directly on the sample in the microcuvette, and a second absorption measurement is performed to compensate for background interference.

19 Claims, 1 Drawing Sheet

ANALYSIS METHOD AND CUVETTE THEREFOR

Figure 1:
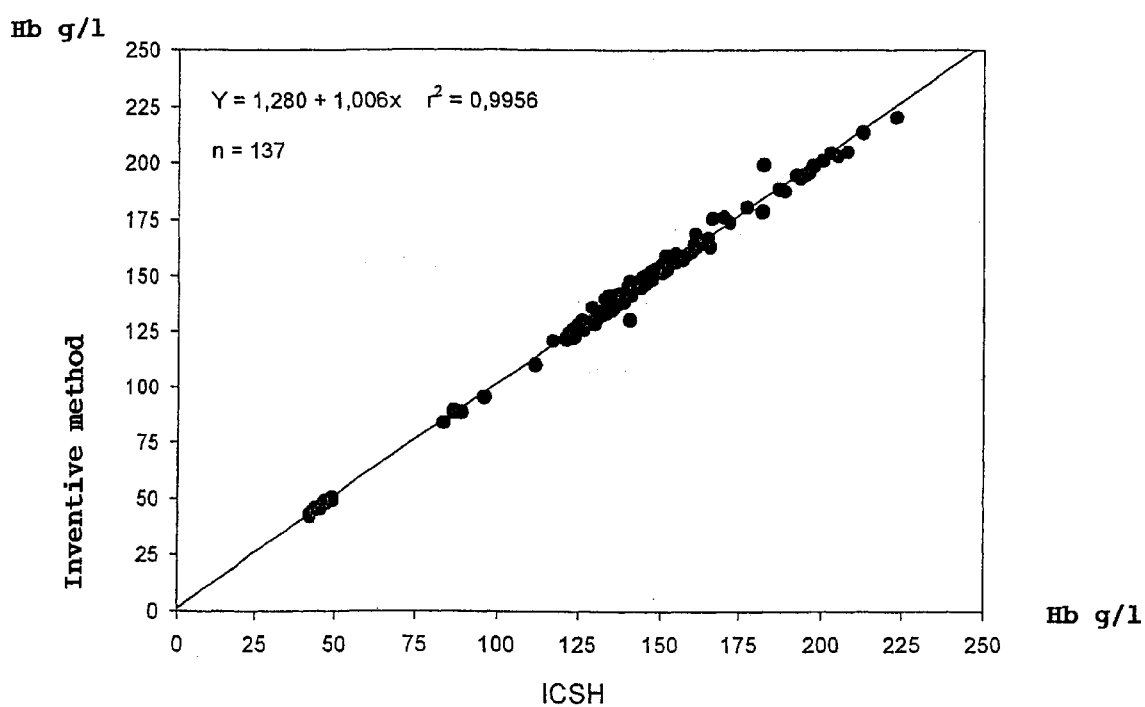

This is a continuation-in-part of U.S. patent application Ser. No. 09/711,939, filed Nov. 15, 2000, now abandoned, which is a continuation of International Application No. PCT/SE01/01442 that designates the United States of America which was filed on Jun. 25, 2001, and was published in English on Jan. 3, 2002; and claims priority for Swedish Application No. 0002443-0, filed Jun. 28, 2000.

FIELD OF INVENTION

The present invention concerns an analysis method and a cuvette for performing this analysis. Specifically the invention concerns a method for determination of haemoglobin in undiluted whole blood and a disposable cuvette which can be used in this determination.

BACKGROUND ART

A disposable cuvette for sampling a fluid, mixing the sample with a reagent and directly making optical analyses of the sample mixed with the reagent is previously known from U.S. Pat. No. 4,088,448. This known cuvette has several advantages as it i.a. simplifies the sampling procedure, reduces the number of utensils and considerably improves the accuracy of analysis by making the analysing procedure independent of the operating technique of the operator making the analysis. A cuvette construction based on the same principle and with improved flow characteristics is disclosed in the U.S. Pat. No. 5,674,457.

A disposable cuvette developed according to these patents is currently widely used for haemoglobin measurement(Hb determination) of undiluted whole blood. To this end the cuvette cavity has been pre-treated with a reagent, such that when a blood sample is drawn into the cuvette, the walls of the red blood cells are disintegrated and a chemical reaction is initiated. The result of the reaction allows Hb determination by absorption measurement directly through the transparent walls of the cuvette which, in the measuring zone, also called the optical window, has a predetermined and accurately defined distance between the inner surfaces of the opposing planar walls. The measurement method is based on a modified azidmethemoglobin method according to Vanzetti, G., Am.J. Lab.& Clin. Med. 67, 116 (1966).

The spectophotometric measurements are made at 570 and 880 nm. This quantitative measurement method based on dry chemistry has met with considerable success as can be seen in e.g. the article by von Schenck et al in Clinical Chemistry, vol 32, No 3, 1986 as the method gives equal or even superior results in comparison with the results obtained with standardised wet methods for the determination of Hb. The reagent used is comprised of sodium deoxycholate which hemolyses the red blood cells, sodium azide and sodium nitrite, which converts haemoglobin to azidmethemoglobin.

Due to the hygroscopic properties of the reagents used, the shelf life is limited and the storage of the cuvettes in sealed packages including a drying agent is required. Even more troublesome is the fact that, in climates with high humidity, the cuvette has to be used within a few minutes after the removal from the package, as otherwise the reagents will be destroyed and the measurement will be inaccurate and thus useless.

OBJECTS OF THE INVENTION

An object of the present invention is to provide a rapid, quantitative method for the determination of hemoglobin in whole blood.

A second object is to provide a method for the determination of hemoglobin in whole blood, which may be performed in a disposable microcuvette.

A third object is to provide a microcuvette for the determination of hemoglobin in undiluted, whole blood in which method the problems originating from the hygroscopic properties of the reagents are eliminated.

Other objects will be apparent from the following description and the accompanying claims.

SUMMARY OF THE INVENTION

In accordance with the present invention a method for providing such a hemoglobin determination comprises the steps of introducing a sample of undiluted whole blood by capillary action into a disposable microcuvette having at least one cavity for receiving the sample. The cavity includes a dry essentially non-hygroscopic hemolysing agent, which is dissolved by the blood, hemolyses the red blood cells and releases the haemoglobin contained in the blood cells. A first absorption measurement at a wavelength range 490–520 nm is then performed directly on the sample in the microcuvette, and a second absorption measurement is performed to compensate for background interference.

It has thus unexpectedly been found that quantitative determinations of haemoglobin can be performed without the chemical reagents sodium azide and sodium nitrite mentioned above. More specifically, it has been found that quantitative determinations may be performed directly on the hemolysed blood provided that an appropriate hemolysing agent or a mixture thereof is selected.

In accordance with the present invention it has thus been found that the hygroscopic reagents can be eliminated. Furthermore, it has been found that the time for obtaining the analytical determination may be reduced. As the analyses are performed in large amounts in e.g. hospitals and blood banks, the time aspect is important.

BRIEF DESCRIPTION OF THE FIGURE OF THE DRAWINGS

FIG. 1 represents an evaluation of the results obtained according to the present invention compared to the standard ICSH method.

DETAILED DESCRIPTION OF THE INVENTION

The disposable microcuvette used according to the present invention may be of the type disclosed in the U.S. Pat. No. 4,088,448 or preferably in the U.S. Pat. No. 5,674,457 which are hereby incorporated by reference. It may be defined as a unitary body member including at least one cavity with an optical window (measuring zone) wherein two, plane or curved, surfaces facing the cavity are placed at a predetermined distance from one another and thus define a predetermined optical path length. This distance between the surfaces defining the measuring zone is a critical parameter in providing the proper optical path length for the haemoglobin measurement and in a preferred embodiment this distance is between 0.05 and 0.2 mm. The distance between the inner surfaces of the rest of the cavity is preferably in the order of 0.1–2 mm which is effective to permit the sample to enter the cavity by capillary force through the cavity inlet, which is communicating with the exterior of the body member. Furthermore, the cavity has a predetermined fixed volume of less than about 25 $\mu$l. A dried hemolysing agent is coated on the cavity surface. The hemolysing agent is preferably present in excess of the amount required for the hemolysing reaction. No other additives are necessary for the determination according to the inventive method.

The cuvettes according to the present invention may be formed by any suitable material, which allows the formation of the necessary tight tolerance levels. Preferably the cuvette is manufactured by injection moulding of a transparent polymeric material.

A critical feature of the present invention is the hemolysing agent. Specifically, this agent should be essentially non hygroscopic and easily soluble in water or more exactly undiluted whole blood. Furthermore, as it is important that the method gives reproducible results, this agent should preferably have a well defined chemical structure. As the hemolysing agent is preferably introduced into the cuvette cavity as a solution, which is subsequently carefully dried preferably by using heat, it is also suitable that the hemolysing agent is easily soluble in organic solvents which does not destroy the hemolysing agent and which can easily be evaporated at low temperatures. It is therefore preferred that the hemolysing agent should be easily soluble in alcohols, such as methanol.

Another important aspect when selecting the hemolysing agent is that this agent in the dried form, which is present in the ready-to-use microcuvette, permits a rapid and uniform introduction of whole blood into the cuvette. Particularly, the time period for the introduction of the whole blood into the microcuvette should be shorter than the time period required by this blood for dissolving the hemolysing agent in the microcuvette.

A particularly preferred group of hemolysing agents are ionic and non-ionic, surface active substances with hemolysing properties. Examples of such substances are quaternary ammonium salts selected from the group of alkyl triethylammonium salts, alkyldimethylbenzylammonium salts and alkylpyridium salts consisting of: tetradecyltrimethyl ammonium bromide (TTAB), dodecyltrimethyl ammonium chloride, cetyltrimethyl ammonium bromide, hexadecyltrimethyl ammonium bromide, benzalkonium chloride, cetylpyridium chloride and other quaternary ammonium salts, sodium lauryl sulphate, and salts of deoxycholic acid. Particularly suitable hemolysing agents to be used according to the invention are sodium deoxycholate, potassium deoxycholate, calcium deoxycholate, morfolin deoxycholate, cyclohexylammonium deoxycholate and ammonium deoxycholate or combinations thereof. The presently most preferred hemolysing agent which fulfils the requirement of providing a quantitative and rapid determination of hemoglobin is a combination of sodium deoxycholate and ammonium deoxycholate. The amount of ammonium deoxycholate is preferably 20–80% by weight of this combination.

During the experiments resulting in the present invention it was found that the maybe most commonly used group of agents for hemolysing blood, i.e. the saponins which are natural products widely distributed in plants and which are mixtures of different chemical structures, do not give reproducible results in the inventive method. The saponins are powerful hemolysing agents even at very low concentrations.

A critical feature of the inventive method and an important difference in comparison with the known and presently commercially used method for determination of Hb in microcuvettes is also that the absorption measurement has to be performed at another wavelength. Thus it has been found that the absorption determination should be carried out in a range of 490–520 preferably 500–510 nm. The secondary compensatory adsorption measurement is preferably performed in the range 850–910, preferably 860–900 nm.

Measurements for the determination of blood at these wavelengths are disclosed in the U.S. Pat. No. 5,064,282. According to this patent the measurement is made in a reusable cuvette, which contains blood which has previously been hemolysed with saponin. Particularly this method involves placing a drop of blood on a glass slide, stirring the blood with a stick having saponin thereon until translucent and introducing the hemolysed blood into the cuvette.

As regards the potential disturbance of the determination due to the presence of methaemoglobin according to the present invention it is appreciated that such a disturbance will occur in patients having a very rare congenital enzyme abnormality, in some rare variants of normal haemoglobin and after exposure of certain drugs and chemicals, such as phenacetin, nitrates, quinones, chlorate. Perhaps as much as 10–20% methaemoglobin will be present in the blood in these cases, but when they occur it will be sufficiently obvious clinically to indicate the need for using the azide method, i.e. the method currently used in microcuvettes, or the haemoglobincyanide method (a reference ICSH method) instead. In this context it should be added that this problem, if any, is also present with the traditional and universally accepted oxyhaemoglobin method. Also high concentrations of carboxyhaemoglobin in heavy smokers and sulfhaemoglobin may cause disturbances.

Photometers suitable for performing these measurements may be obtained by modifying existing photometers with suitable filters and light emitting diodes. According to a preferred embodiment of the invention a photometer measures the absorbance at the two wavelengths and a built-in micro processor calculates, according to a programmed algorithm, the total concentration of hemoglobin in blood.

The following non limiting example illustrates the inventive method.

A hemolysing agent consisting of equal parts of sodium and ammonium deoxycholate was dissolved in methanol and introduced into a disposable microcuvette having the above construction. The methanol was then evaporated.

In a comparison between the inventive method performed in microcuvettes containing only the dried mixture of sodium and ammonium deoxycholate and the method for determination of hemoglobin in the known, currently used HemoCue microcuvettes containing the sodium nitrite/sodium azide reagent as well as sodium deoxycholate, it was found that the time period for hemolysing the blood was about 15 seconds shorter with the preferred hemolysing agent according to present invention. Particularly the period for hemolysing the dried hemolysing agent present in the microcuvette should be less than 40 seconds. This permits a further reduction up to 25% of the total time of the hemoglobin determination which may be advantageous in busy hospitals and in other situations where may determinations are made.

In a corresponding comparison concerning the stability with regard to humidity it was found the stability of the microcuvettes including the deoxycholate mixture mentioned above was 24 hours in air of 45° C. and 80% relative humidity which should be compared with about 2 minutes for the commercially available HemoCue microcuvettes under the same conditions.

An evaluation of the new method with this hemolysing mixture (and without any other chemicals) in comparison with the standard ICSH method is disclosed in FIG. 1. The evaluation was made under laboratory conditions. As can be seen the agreement between the methods is very good.

The spectophotmetric absorption measurements were made at about 570 nm for the known method and about 505 nm for the new method. For both methods compensatory measurements were made at 880 nm.

The foregoing has been a description of a certain preferred embodiment of the present invention, but it is not intended to limit the invention in any way. Rather, many modifications, variations, and changes in details may be made within the scope of the present invention.

We claim:

1. A method for quantitative haemoglobin determination in undiluted whole blood comprising the steps of:
   introducing a sample of undiluted whole blood containing red blood cells having haemoglobin therein by capillary action into a disposable microcuvette having at least one cavity for receiving the sample, the cavity including an essentially non-hygroscopic hemolysing agent in a dry form, the cavity being essentially free of azide and nitrite, whereby the hemolysing agent is dissolved in the whole blood, the agent hemolyses the red blood cells and the haemoglobin contained in the blood cells is released;
   performing a first absorption measurement at a wavelength range directly on the hemolysed sample in the cuvette,
   further conducting a second absorption measurement on the hemolysed sample to compensate for background interference, and
   analyzing the results of the absorption measurements and determining the concentration of haemoglobin in the whole blood sample.

2. The method according to claim 1 wherein the hemolysing agent is soluble in organic solvents.

3. The method according to claim 2 wherein the organic solvent is an alcohol.

4. The method according to claim 3 wherein the hemolysing agent present in the microcuvette permits a rapid introduction of whole blood into the cuvette.

5. The method according to claim 2 wherein the hemolysing agent U present in the microcuvette, permits a rapid introduction of whole blood into the cuvette.

6. The method according to claim 1 wherein the hemolysing agent present in the microcuvette, permits a rapid introduction of whole blood into the cuvette.

7. The method according to claim 6 wherein the time for the introduction of whole blood into the microcuvette is shorter than the time required for dissolving the hemolysing agent.

8. The method according to claim 1 wherein the hemolysing agent is selected from the group consisting of ionic and nonionic, surface active substances.

9. The method according to claim 1 wherein the hemolysing agent is selected from the group consisting of salts of deoxycholic acid and quaternary ammonium salts.

10. The method according to claim 1 wherein the hemolysing agent is selected from the group consisting of sodium deoxycholate, potassium deoxycholate, calcium deoxychoholate, morfolin deoxycholate, cyclohexylammonium deoxycholate, ammonium deoxycholate and mixtures thereof.

11. The method according to claim 1 wherein the hemolysing agent essentially consists of a mixture of sodium deoxycholate and ammonium deoxycholate.

12. The method according to claim 11 wherein the amount of ammonium deoxycholate is between 20 and 80 percent by weight.

13. The method according to claim 1 wherein the second absorption measurement is performed in the range of 850–910 nm.

14. The method according to claim 1 wherein the first absorption measurement is performed in the range of 500–510 nm.

15. The method according to claim 1 wherein the second absorption measurement is performed in the range of 860–900 nm.

16. Disposable microcuvette for spectrophotometric determination of haemoglobin in undiluted whole blood, wherein the microcuvette comprises a cavity containing a dried, non-hygroscopic hemolysing agent or a combination of said agents, provided that the cavity is essentially free from azide and nitrite, wherein the hemolysing agent is a salt of deoxycholic acid.

17. The disposable microcuvette according to claim 16, wherein the hemolysing agent is selected from the group consisting of sodium deoxycholate, potassium deoxycholate, calcium deoxycholate, morfolin deoxycholate, cyclohexylammonium deoxycholate, ammonium deoxycholate and mixtures thereof.

18. The disposable microcuvette according to claim 16, wherein the hemolysing agent essentially consists of a mixture of sodium deoxycholate and ammonium deoxycholate.

19. The disposable microcuvette according to claim 18, wherein the amount of ammonium deoxycholate is between 20 and 80 percent by weight of the mixture.

* * * * *